United States Patent [19]

Mori et al.

[11] Patent Number: 5,316,905
[45] Date of Patent: May 31, 1994

[54] CULTURE MEDIUM SUPPLYING METHOD AND CULTURE SYSTEM

[75] Inventors: Junichi Mori; Masaaki Abe, both of Tokyo, Japan

[73] Assignee: Suzuki Shokan Co., Ltd., Tokyo, Japan

[21] Appl. No.: 811,296

[22] Filed: Dec. 20, 1991

Related U.S. Application Data

[63] Continuation-in-part of Ser. No. 478,742, Feb. 12, 1990, abandoned, which is a continuation of Ser. No. 99,978, Sep. 23, 1987, abandoned.

[30] Foreign Application Priority Data

Sep. 29, 1986 [JP] Japan .................................. 61-228380
Aug. 19, 1987 [JP] Japan .................................. 62-205510

[51] Int. Cl.[5] .......................... C12Q 3/00; C12M 3/00
[52] U.S. Cl. ..................................... 435/3; 435/240.1; 435/284; 435/289; 435/313
[58] Field of Search ................. 435/3, 240.1, 240.23, 435/240.241, 240.242, 284, 286, 289, 313, 315, 813, 285

[56] References Cited

U.S. PATENT DOCUMENTS

| | | | |
|---|---|---|---|
| 4,804,628 | 2/1989 | Cracauer et al. | 425/240.242 |
| 4,889,812 | 12/1989 | Guinn et al. | 435/285 |
| 4,973,558 | 11/1990 | Wilson et al. | 435/313 |

FOREIGN PATENT DOCUMENTS

| | | | |
|---|---|---|---|
| 0263634 | 4/1988 | European Pat. Off. | |
| 1058582 | 3/1986 | Japan | 435/284 |
| 0685688 | 9/1979 | U.S.S.R. | 435/289 |
| 0734281 | 5/1980 | U.S.S.R. | 435/284 |

*Primary Examiner*—Michael G. Wityshyn
*Assistant Examiner*—William H. Beisner
*Attorney, Agent, or Firm*—Pollock, Vande Sande & Priddy

[57] ABSTRACT

A culture system comprising at least first and second culture medium tanks including a gas phase, a culture medium phase, at least one gas phase port, and at least one culture medium port. At least one culture vessel. First switching-over members have a plurality of culture medium flow passages connected between the tanks and the culture vessels. The culture medium phase of the first tank flows through the passages to the culture medium phase of the second tank via the culture vessel. Switching-over of the culture medium flow passages causes the culture medium phase of the second tank to flow through the passages to the culture medium phase of the first tank via the culture vessel. Gas supply section comprises at least two pressure chambers and at least two gas ports connected to the pressure chambers. Second switching-over members have formed therein a plurality of gas flow passages allowing a gas to flow from the gas control section to the gas phase in the first and second tanks. Switching-over of the gas flow passages causes the gas flow to switch between the tanks. The gas control section includes gas pressure regulating members, gas flow rate regulating members and gas component regulating members. Gas source switching-over members are included.

19 Claims, 7 Drawing Sheets

CULTURE MEDIUM SUPPLYING METHOD AND CULTURE SYSTEM

BACKGROUND OF THE INVENTION

This application is a continuation-in-part of application Ser. No. 07/478,742 filed Feb. 12, 1990, now abandoned, which was a continuation of application Ser. No. 07/099,978 filed Sep. 23, 1987, now abandoned.

This invention relates to a method of supplying a culture medium into a culture vessel for cultivating culture cells and to a culture system for carrying out the method of supplying the culture medium.

Recently, culture systems have been earnestly investigated for the purpose of reproducing biological cells in artificial vessels. Such a culture system can produce an artificial environment for the biochemical reaction in a living body and makes it possible to produce substances, such as immunoglobulin, which are beneficial for human society, continuously in large quantities with a higher efficiency. Such substances have been produced by cultivating inoculation culture substances in living animal bodies such as mice and the like.

Jar fermentor, roller bottle, membrane cultivating methods and the like have been known. Culture systems for these methods have been studied to improve them.

FIG. 1 is a block diagram schematically illustrating one exemplary arrangement of a prior art culture system using membranes.

This culture system includes a culture vessel (for example, a hollow fiber filter) using the membranes and a culture medium tank from which a predetermined culture medium is supplied into the culture vessel in which required cells are cultivated.

In FIG. 1, the hollow fiber filter in culture vessel 11 mainly consists of a flow passage 11a for passing the culture medium supplied from the culture medium tank 12, and culture chambers 11b in which the cells are cultivated. Moreover, the flow passages 11a and the culture chambers 11b are partitioned by the membranes capable of cutting off predetermined molecular weights. Such partitions 11c serve to prevent cells cultivated in the culture chambers 11b from entering the flow passage 11a but permit the culture medium flowing in the flow passage 11a to be supplied into the culture chambers 11b and waste matters to be removed from the culture chambers 11b into the flow passage 11a.

Moreover, the culture medium stored in the culture medium tank 12 has been adjusted to have predetermined values of pH (hydrogen ion concentration), DO (dissolved oxygen concentration) and the like. Moreover, culture systems have been known, whose culture medium tanks include means for automatically adjusting pH, DO and other parameters.

A driving source 14 serves to supply the culture medium from the culture medium tank 12 into the culture vessel 11. Therefore, the culture medium enters one side of the flow passage 11a of the culture vessel 11 and leaves the other side of the culture vessel 11. As the driving source, peristaltic pumps, bellow pumps or magnetic pumps have been used.

In using a peristaltic pump as the driving source 14, sliding means scrapes outer surfaces of a silicon tube and the like of the pump to drive a culture medium in the silicon tube for supplying the culture medium into a culture vessel 11.

In using a bellows pump as the driving source 14, a culture medium stored in a bellows is fed from the bellows by its extension and contraction for supplying the culture medium into a culture vessel 11.

In using a magnetic pump as the driving source 14, a magnetic rotor provided in the pump is rotated by a magnetic force from the outside of the pump to drive a culture medium by the rotating force of the magnetic rotor for supplying the culture medium into a culture vessel 11.

When a peristaltic pump is used as the driving source, however, the sliding means which drives the culture medium often damages the tube when it is in use for a long period of time. As a result, the culture medium is not supplied into the culture vessel but flows away to places other than the culture vessel. Alternatively, the culture chambers are contaminated when the tube is damaged.

In order to avoid such problems, it is required to displace the sliding means to new positions periodically as maintenance.

Moreover, as the sliding means scrapes the tube, worn tube material is mixed into the culture medium. Therefore, it is required to filter the culture medium mixed with the worn tube material.

In using a peristaltic pump, pulsations occur in the culture medium being fed into the culture vessel resulting from the constructional characteristics of the peristaltic pump, so that the supply of the culture medium into the culture vessel is disturbed.

In using a bellows pump or a magnetic pump, particular maintenance and operation of the pump are needed although the disadvantages in the peristaltic pump are mitigated.

In hitherto used culture systems, particularly those using ultrafiltration membranes, the direction of flow of the culture medium in the flow passage in the culture vessel is fixed. Therefore, when anchored cells are used for cultivation, the cells anchored to the culture chamber on a side upstream of the flow of the medium in the chamber contact the culture medium which has been adjusted in pH values or the like, with the result that the cells on a side downstream of the flow tend to include waste matters produced by metabolism of the cells anchored on the side upstream of the flow. On the other hand, suspension cells are likely to be carried onto the side downstream of the flow by a driving action of the flow. Accordingly, a locally uneven cultivating environment is produced so that cultivating density of cultivated substances becomes uneven.

SUMMARY OF THE INVENTION

It is a primary object of the present invention to provide a method of supplying a culture medium into a culture vessel which eliminates all the disadvantages of the prior art as above described and is able to supply the culture medium stably with constant flow amounts for a long period of time.

It is another object of the invention to provide a culture system which is able to carry out the method described above and which has a construction eliminating damage of parts.

In order to achieve the primary object of the invention, in the method of supplying a culture medium into a culture vessel according to the invention, the culture medium is fed into a culture vessel under a pressure difference of a gas.

The term "being fed under pressure difference of a gas" used herein is intended to mean that a culture medium in a tank is subjected to a higher pressure to force the medium out of the tank into a system lower in pressure than that in the tank and/or a system is made lower in pressure than that in the tank including the culture medium to suck the medium from the tank into the system.

In carrying out the method of the invention, it is preferable to change directions of the culture medium fed into the culture vessel with time intervals. Namely, the culture medium is caused to flow into one side of the culture vessel and is drained from the other side of the culture vessel for a certain period of time, and then the culture medium is caused to flow into the other side of the vessel and is drained from the one side of the vessel, thereby changing the directions of the flow of the culture medium with time intervals at will.

The time for changing the directions of the flow of the culture medium is preferably determined depending upon kinds of cultivated substances, for example, tissue cells and the like forming skins and internal organs of animals.

In order to accomplish the second object of the invention, the culture system according to the invention comprises a culture vessel, a culture medium supply assembly for supplying a culture medium into the culture vessel, and a gas pressure supply assembly for supplying gas pressure for feeding the culture medium into the culture vessel with the aid of pressure differences of the gas.

The culture medium supply assembly comprises a culture medium adjusting tank having means for adjusting pH, DO values and the like, and first and second tanks for supplying, collecting and replenishing the culture medium. The culture medium supply assembly further comprises flow passages for connecting these tanks and switching-over means for selectively making these flow passages effective, according to requirements. Moreover, the culture medium supply assembly comprises flow passages for making connections between the culture medium adjusting tank and one end of the culture vessel. Flow passages, between the culture medium adjusting tank and the other end of the culture vessel. Flow passage switching-over means are provided for making effective either of the flow passages. Further, the culture medium supplying assembly comprises flow passages for connecting the culture vessel with first and second culture medium supply and collection tanks. Flow passage switching-over means are also provided for switching over the flow passages for collecting the culture medium from the culture vessel into one culture medium supply and collection tank when the flow passage between the other culture medium supply and collection tank and the culture medium adjusting tank is effective. The above flow passage switching-over means are preferably controlled by a control section described below.

Furthermore, the gas pressure supply assembly comprises a gas pressure producing section having first and second pressure chambers and a compressor for producing pressures in the first and second pressure chambers different from each other, such that, for example, the pressure in the first pressure chamber is higher than the pressure in the second pressure chamber. Moreover, the gas pressure supply section comprises a plurality of gas supply flow passages for feeding the gas from the respective pressure chambers into required locations of the culture system including the culture medium supply assembly, and switching-over means for switching over these gas flow passages.

According to the method of the invention, the culture medium is fed under a pressure difference into the culture vessel. Therefore, by keeping the pressure difference at a constant value, the flow rate of the culture medium can be maintained at a constant value corresponding to the pressure difference, thereby preventing pulsations in the culture medium. Further, by changing the pressure difference, the amount of the culture medium to be supplied can be controlled.

Moreover, by changing the kinds and components of the gas which is a pressure source for supplying the culture medium, the amount of gas dissolved in the culture medium can be easily controlled.

In the event that directions of the culture medium fed into the culture vessel are changed with time intervals, a direction of flow of the culture medium in the culture vessel is reversed. This change in flow direction stirs the culture medium in the culture chambers of the culture vessel and changes the cultivating environment so as to make uniform cultivating conditions in the culture chambers uniform.

According to the culture system of the invention, the culture medium is supplied under a pressure difference of gas pressures in the gas pressure supply assembly from the culture medium supply assembly into the culture vessel.

In more detail, when a passage between the first pressure chamber, the first culture medium supply and collection tank, the culture medium adjusting tank, the culture vessel, the second culture medium supply and collection tank and the second pressure chamber is effectively formed, the culture medium is fed under a pressure difference between the first and second pressure chambers from the first culture medium supply and collection tank through the culture medium adjusting tank and the culture vessel into the second culture medium supply and collection tank.

Moreover, the culture system according to the invention comprises flow passages for connecting the culture medium adjusting tank and one end of the culture vessel and for connecting the culture medium adjusting tank and the other end of the culture vessel. Also included in the invention is flow passage switching-over means for making effective either of these flow passages. Further flow passage switching-over means are provided for switching over the flow passages for connecting one end of the culture vessel opposite to the end being supplied with the culture medium to one of the culture medium supply and collection tanks, thereby effecting cultivation of the cells while changing the direction of flow of the culture medium in the culture vessel in the reverse direction with time intervals.

In order that the invention may be more clearly understood, preferred embodiments will be described, by way of example, with reference to the accompanying drawings.

DESCRIPTION OF THE PREFERRED EMBODIMENTS

Figure 2A:
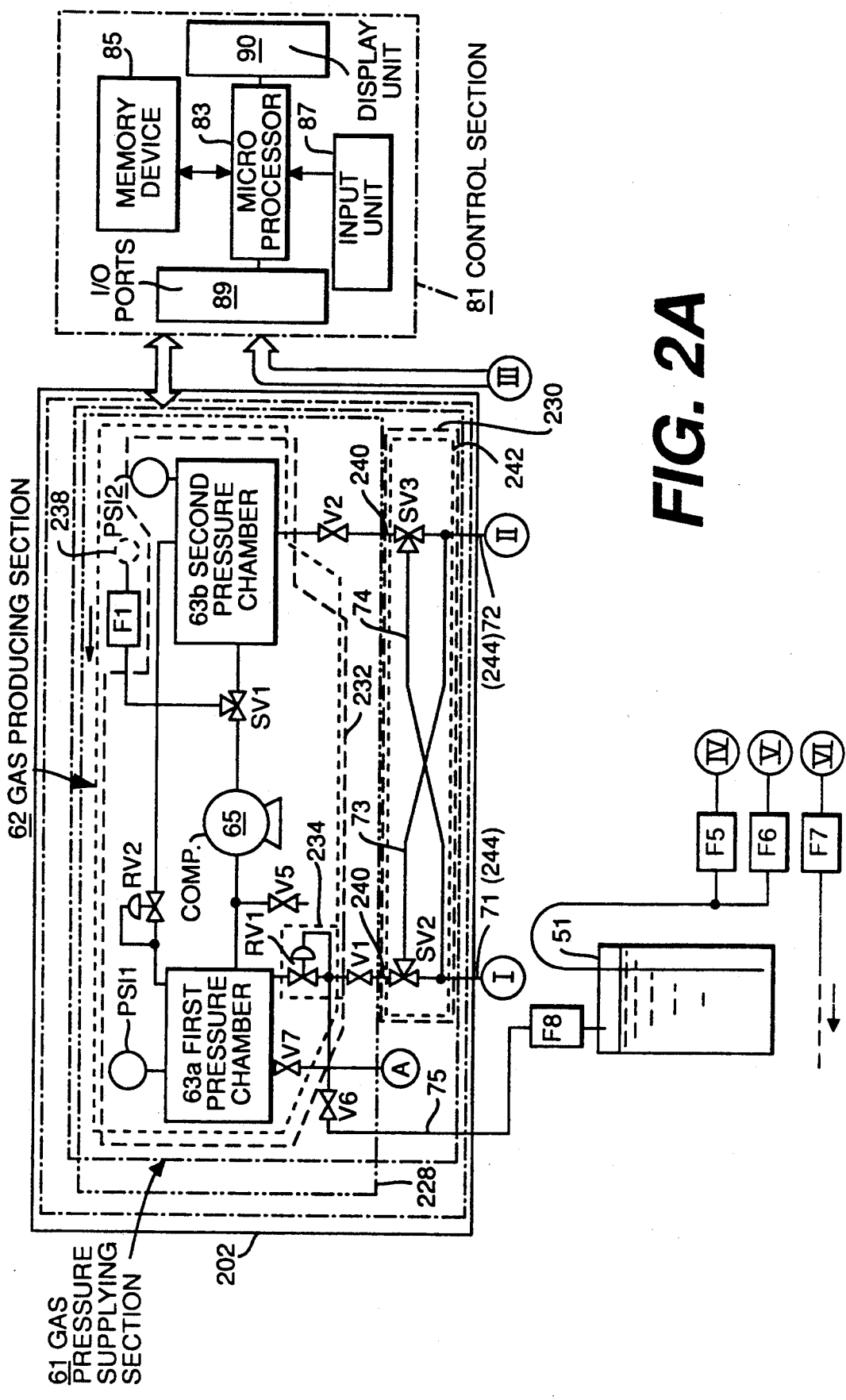
FIGS. 2A to 2E are block diagrams illustrating respective parts of a principal portion of one embodiment of the culture system according to the invention.
Figure 2B:
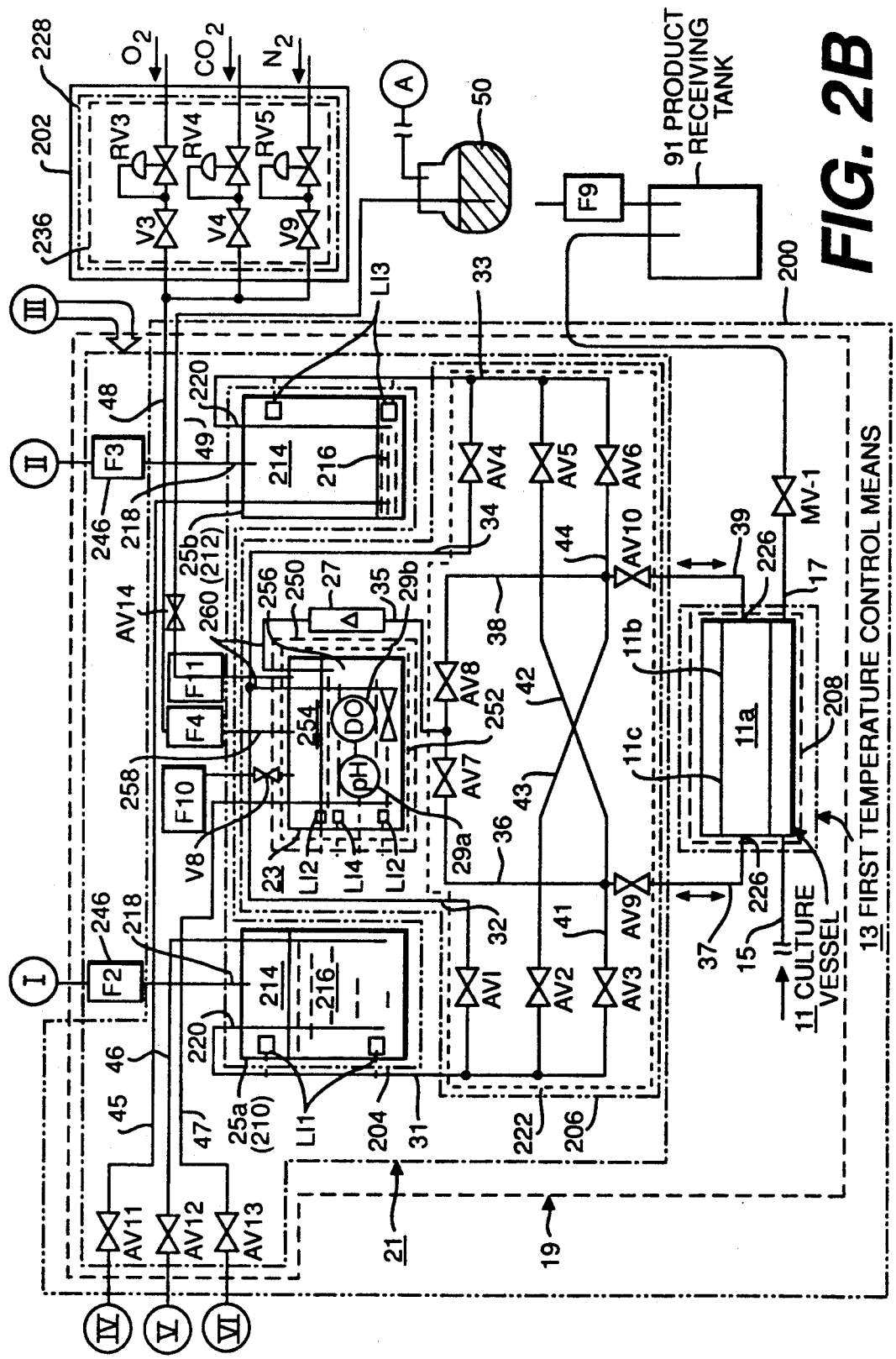

FIGS. 2A and 2B are block diagrams illustrating respective principal parts of a culture system according to one embodiment of the invention. These block diagrams are drawn schematically o an extent such that the invention is understood, omitting sections for sterilization, cleaning and maintenance and the like for the sake of clarity. The arrangement of the respective components is not limited to that shown in FIGS. 2A and 2B. The Roman numerals I, II, and III, IV, V, VI shown in FIG. 2A are connected to the corresponding numerals I, II, III, IV, V, and VI shown in FIG. 2B.

Culture Vessel

Figure 1:
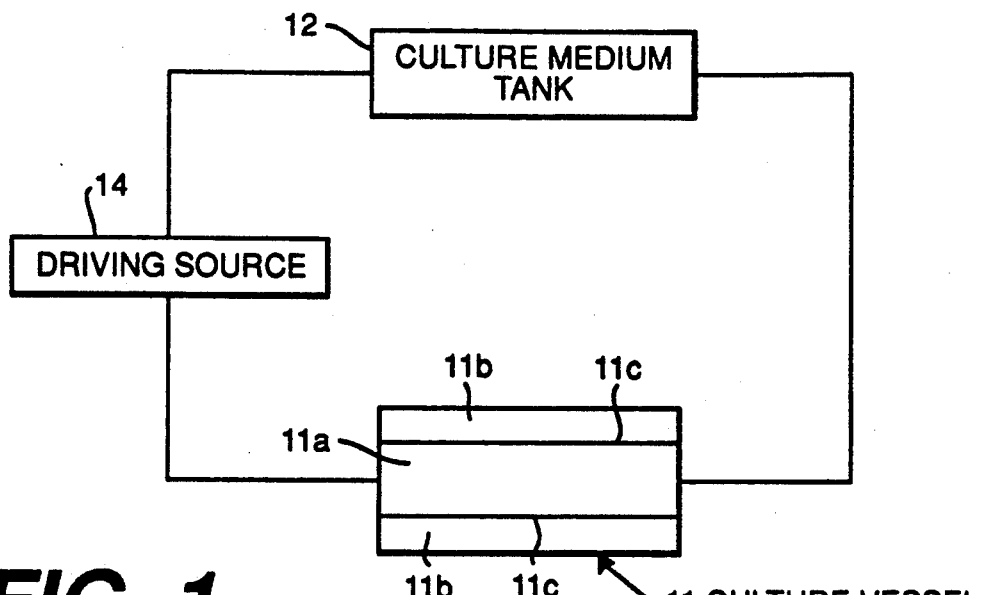
FIG. 1 is a block diagram schematically illustrating an exemplary arrangement of a culture system of the prior art.

A culture vessel 11 of this embodiment shown in FIG. 2B uses, for example, a publicly known hollow fiber. As explained with reference to FIG. 1, the hollow fiber filter 11 has a passage 11a for a culture medium, culture chambers 11b and partition walls 11c therebetween for cutting off material of a predetermined molecular weight. In the culture system of this embodiment, there is provided first temperature control means 13 constructed, for example, by a water jacket in order to maintain the hollow fiber filter at a desired environmental temperature.

The hollow fiber filter 11 further comprises an inlet 15 for supplying an inoculation culture substance and an outlet 17 for taking products out of the hollow fiber filter 11. A product receiving tank 91 is connected through a manually operable valve MV-1 to the outlet 17.

Culture Medium Supply Assembly

Reference numeral 21 denotes a culture medium supply assembly. The culture medium supply assembly 21 comprises a culture medium adjusting tank 23 for adjusting pH, DO and the like of the culture medium; first and second culture medium supply and collection tanks 25a and tank 25b, (also referred to hereinafter as "first tank 25a" and "second tank 25b", respectively. Culture medium flow passages are provided between the culture vessel 11, the culture medium. The present invention also comprises adjusting tank 23 and the first and second tanks 25a and 25b in predetermined relations, later described in detail. Switching-over means is provided for switching over these flow passages according to purposes (later described in detail). In order to detect upper and lower limit levels of the stored culture medium, the adjusting tank 23 includes level gages LI2, and the first and second tanks 25a and 25b include level gages LI1 and L13, respectively.

In this embodiment, the switching-over means consists of valves (later described in detail) provided in a predetermined manner in the plurality of flow passages in the culture medium supply section 21, and a control section 81 (see FIG. 2A) including means for closing and opening these valves.

In this embodiment, the valves are driven by gas pressure from a gas pressure supply section 61 according to instructions from the control section 81. However, the driving of the valves is not limited to this feature. They may be magnetically driven from the control section 81. The valves are designated by AV-1-AV3 in FIG. 2B.

Connections of the culture medium flow passages between the above vessel and tanks will be explained hereinafter.

The first tank 25a and the culture medium adjusting tank 23 are connected through the flow passage 31, the valve AV1 and the flow passage 32. The second tank 25b and the culture medium adjusting tank 23 are connected through the flow passage 33, the valve AV4 and the flow passage 34.

The culture medium adjusting tank 23 and one end of the flow passage 11a of the culture vessel 11 are connected by the flow passage 35 having a flow meter 27, the flow passage 36 having a valve AV7 and the flow passage 37 having a valve AV9. Moreover, the culture medium adjusting tank 23 and the other end of the flow passage 11a of the culture vessel 11 are connected by the flow passage 35 having a flow meter 27, the flow passage 38 having a valve AV8 and the flow passage 39 having a valve AV10.

The flow passages 31 and 36 are connected by the valve AV3 and the flow passage 41, and the flow passages 33 and 36 are connected by the valve AV5 and the flow passage 42.

Moreover, the flow passages 31 and 38 are connected by the valve AV2 and the flow passage 43, while the flow passages 33 and 38 are connected by the valve AV6 and the flow passage 44.

A culture medium replenishing tank 51 separately prepared is connected through a sterilization filter F5, a valve AV11 and a flow passage 45 to the second tank 25b and is further connected through a sterilization filter F6, a valve AV12 and a flow passage 46 to the first tank 25a.

In this embodiment, the culture medium adjusting tank 23 is supplied through a flow passage 48 with oxygen, carbon dioxide or nitrogen and is further supplied through a flow passage 49 with an alkaline solution (7.5% $NaHCO_3$ solution in this embodiment) through a reservoir tank 50 as shown in FIG. 2B, thereby adjusting pH or DO in the tank 23 by the gas and chemical liquid. The tank 23 includes a sensor 29a for a pH meter and a sensor 29b for a dissolved oxygen meter as shown in FIG. 2B. It can be supposed that the introduction of the oxygen, carbon dioxide or nitrogen gas sometimes results in a change in the gas pressure in the culture medium adjusting tank 23, with the result that the surface level of the medium in the tank 23 is changed. In order to provide for such an extraordinary change in surface level, the culture medium adjusting tank 23 comprises a level gage LI4 and a valve V8 for venting. The culture medium adjusting tank 23 also serves as a buffer for restraining change in flow rate when switching over the flow passages.

Unused culture medium can be removed from the culture medium adjusting tank 23 through a flow passage 47, a valve AV13 and a sterilization filter F7.

In this embodiment, moreover, the culture medium supply assembly and the culture vessel 11 as above described are accommodated in a constant temperature bath 19 having second temperature control means.

Gas Pressure Supply Assembly

Reference numeral 61 denotes a gas pressure supply assembly. This gas pressure supply assembly 61 includes therein a gas pressure producing section 62 having first and second pressure chambers 63a and 63b and a compressor 65 for generating different gas pressures in the chambers 63a and 63b. An external gas, for example air, is introduced through a filter F1 and a magnetic three-way valve SV1 into the compressor 65 in which the gas is compressed and fed into the first pressure chamber 63a in which the compressed gas is stored. The remaining passage of the three-way valve SV1 is connected to the second pressure chamber 63b. Therefore, the pressure in the first pressure chamber is higher than that in the second pressure chamber.

Moreover, the first and second pressure chambers 63a and 63b are provided with pressure gauges PSI1 and PS12, each having pressure switches, and adapted to be connected by a primary pressure regulating valve RV2. These pressure chambers can be set at predetermined pressures in order to supply gas pressures from these pressure chambers for feeding the culture medium under a pressure difference. When the pressure in the first pressure chamber 63a arrives at a predetermined value, the pressure in the chamber 63a is regulated by the primary pressure regulating valve RV2. If the pressure in the first pressure chamber 63a becomes lower than the predetermined value, the magnetic three-way valve SV1 is switched over onto the air introducing side (filter F1 side) to replenish the air in the pressure chamber 63a until the pressure arrives at the predetermined value. When the pressure in the second pressure chamber 63b becomes lower than the predetermined value, the three-way valve SV1 is also switched over onto the air introducing side to introduce the external air once into the first pressure chamber 63a. Thereafter, excess air in the first pressure chamber 63a is fed through the primary pressure regulating valve RV2 into the second pressure chamber 63b.

Between the first pressure chamber 63a and the first tank 25a of the culture medium supply assembly 21, there is provided a gas flow passage 71 having a pressure regulating valve RV1, a magnetic valve V1, a magnetic three-way valve SV2 and a sterilization filter F2. Between the second pressure chamber 63b and the second tank 25b, there is provided a gas flow passage 72 having a valve V2, a three-way valve SV3 and a filter F3. Moreover, the three-way valve SV2 and the gas flow passage 72 are connected by a gas flow passage 73, and the three-way valve SV3 and the gas flow passage 71 are connected by a gas flow passage 74.

With this arrangement, one culture medium supply and collection tank 25a or 25b of the culture medium supply section is connected to the first pressure chamber 63a, while the other culture medium supply and collection tank 25b or 25a is connected to the second pressure chamber 63b so that a pressure difference is provided between the supply and collection tanks 25a and 25b to enable the culture medium to be fed under pressure difference into either of the tanks.

In such an arrangement of this embodiment, by switching over the three-way valves SV2 and SV3, the culture medium supply and collection tanks 25a and 25b can be changed to be connected to the second and first pressure chambers 63b and 63a, whereby gas flow passage switching-over means for switching over the gas flow passages is realized by the three-way valves SV2 and SV3.

The gas for feeding the culture medium under pressure has been explained as the air in the above embodiment. However, there is often a case that the amount of dissolved gas in the culture medium to be used for cultivating greatly affects the proliferation of cells or formation of products depending upon kinds of culture substances such as cells. For example, there are two cases, that a dissolved oxygen amount of a culture medium is more than equilibrium dissolved oxygen amount under the atmospheric pressure, and that the dissolved oxygen amount is less than the equilibrium dissolved oxygen amount. There are culture substances for which the former case is the better environment and others for which the latter is preferred.

When such culture substances are cultivated, it is preferable to determine the dissolved oxygen amount of a culture medium to be used which is appropriate for the culture substances.

In order to fulfill such a requirement, the method for supplying a culture medium uses a gas for feeding the medium under a pressure difference so that, for example, the equilibrium dissolved oxygen amount of the medium can be easily controlled by changing the gas to be used or components of the gas. For example, with a culture substance preferring a dissolved oxygen amount greater than the equilibrium dissolved oxygen amount at atmospheric pressure, air mixed with oxygen at a high concentration is supplied through the filter F1 into the gas pressure producing section shown in FIGS. 2A and 2B to fulfill the requirement. In contrast thereto, for a culture substance preferring a dissolved oxygen amount which is less than the equilibrium dissolved oxygen amount, for example, the air including oxygen at a low concentration obtained by diluting with nitrogen gas may be supplied.

Control Section

The culture system according to the invention comprises a control section for controlling the respective components above described. As the control section can be constructed according to the control technique of the prior art, it will be briefly explained hereinafter.

The control section 81 shown in FIG. 2A comprises, for example, a microprocessor 83, a memory device 85 for storing feeding directions of culture mediums, programs of culture conditions and the like, an input unit 87 for instructing mode selection and change of the feeding directions and culture conditions, input and output (I/O) ports 89 for reading pressure data of the first and second pressure chambers, flow rates of culture mediums, data of pH, DO and the like, data of amounts of culture mediums in the respective tanks and the like, and outputting instruction signal for modifying the pressure, pH, DO and the like and operating the respective values on the basis of these data, and a display unit 90 for displaying various messages.

Operation of the Culture System

The operation of the culture system will be explained hereinafter. The operation is effected in the following sequence (1)–(6). However, the present invention is of course not limited to this sequence. Moreover, the following numerical parameters are only by way of example, and could be modified according to kinds of inoculation culture substances:

(1) Sterilization;

(2) Supply of culture medium to the culture medium supply assembly;
(3) Adjusting the culture medium;
(4) Cells inoculation into the culture vessel;
(5) Supplying the culture medium to the culture vessel
(6) Sampling of Culture Substances and the Like During Period of Cultivating.

In this embodiment, moreover, hollow fiber filter cartridges having a molecular weight cut off at 30000 which are manufactured by Grace Co. in the United States under the trade name of "Vitafiber II", are used for the culture vessel.

(1) Sterilization

Before the cultivation of cells, the tanks 23, 25a and 25b and the flow passages inside the zone bounded by the sterilization filters F2, F3, F5, F6, F7, F9, F10 and F11 associated with the culture medium supply section 21 are sterilized by steam at any suitable temperature, for example, 120° C. for a predetermined period of time, for example, 30 minutes.

(2) Supply of Culture Medium to the Culture Medium Supply Assembly

After sterilization, the culture medium is supplied from the culture medium replenishing tank into the culture medium supply section. In this case, the culture medium is first replenished from the replenishing tank 51 into one of the supply and collection tanks, for example, the first tank 25a. Thereafter, the culture medium is fed through the culture medium adjusting tank 23 into the other supply and collection tank or the second tank 25b.

The valve V1 is then opened and the gas pressurized or adjusted by the pressure adjusting valve RV1 is supplied from the first pressure chamber 63a through the flow passage 75 and the sterilization filter F8 into the culture medium replenishing tank 51. On the other hand, the valve V2, the three-way valve SV3 and valves AV6, AV8 and AV1 are operated respectively to make effective the passage of the second pressure chamber 63b, the gas flow passage 72, the second tank 25b, the flow passage 33, valve AV6, the flow passages 44 and 38, the valve AV8, the flow passage 35, the flow meter 27, the culture medium adjusting tank 23, the flow passage 32, the valve AV1 and the flow passage 31, thereby forming a pressurized feeding system through the culture medium replenishing tank 51, the first and second tanks 25a and 25b, and the culture medium adjusting tank 23. After the formation of the feeding system, the valve AV12 is opened to supply the culture medium from the supply tank 51 through the flow passage 46 into the first tank 25a, and further the culture medium is fed under pressure difference from the first tank 25a through the adjusting tank 23 into the second tank 25b. The amount of the culture medium in the second tank 25b is monitored by means of the level gauge LI3. When the liquid surface of the supplied culture medium arrives at the lower limit level of the level gauge LI3, the valves AV1, AV6 and AV8 are closed upon detecting it. In order to feed the culture medium under a pressure difference from the supply tank 51 into the first tank 25a continuously, the three-way valve SV3 is switched over onto the side of the flow passage 74 to make effective the passage of the second pressure chamber 63b, the valve V2, the three-way valve SV3, the flow passages 74 and 71, the filter F2, the first tank 25a, the flow passage 46 and the valve AV12. The liquid surface of the culture medium in the first tank 25a is monitored by the level gauge L1. When the liquid surface arrives at the upper limit level of the gauge LI1, the valves AV12 and AV6 are closed upon detecting it.

Thereafter, the valve V1 and the three-way valve SV2 are actuated to supply the gas pressure in the first pressure chamber 63a adjusted to a predetermined pressure by the pressure adjusting valve RV1 into the first tank 25a through the gas flow passage 71. (The gas pressure adjusted to the predetermined pressure of the pressure adjusting valve RV1 is referred to sometimes as "first gas pressure".) Moreover, the valve V2 and the three-way valve SV3 are actuated to supply the gas pressure in the second pressure chamber 63b into the second tank 25b through the gas flow passage 72. (The gas pressure in the second pressure chamber to be supplied into the second tank 25b is referred to sometimes as "second gas pressure".) Further, the valves AV1, AV8 and AV6 are opened to feed the culture medium in the first tank 25a under pressure difference into the second tank 25b through the culture medium adjusting tank 23. The amount of the culture medium in the adjusting tank 23 is monitored by means of the level gauge LI2.

(3) Adjusting the Culture Medium

In the culture medium adjusting tank 23, respective parameters such as the pH, DO and the like of the medium are measured by means of respective sensors 29a and 29b. These measured results are fed into control section 81 and if values of these parameters are out of range of values suitable for culture cells, the culture medium is treated so as to bring the values into a predetermined range. If it is required to replenish oxygen for DO value from a result of measuring dissolved oxygen by the dissolved oxygen meter, oxygen is replenished through the flow passage 48 into the culture medium adjusting tank 23. On the other hand, if it is required to lower the dissolved oxygen amount, nitrogen is replenished through the flow passage 48 into adjusting tank 23. If it is required to raise the pH value from a result of measuring the pH value by the pH meter, an alkaline solution in the reservoir tank 50 is supplied through the flow passage 49 into the adjusting tank 23. If it is required to lower the pH value, $CO_2$ gas is supplied through the flow passage 48 into the adjusting tank 23. In case of lowering the pH value, moreover, an acid aqueous solution may be supplied instead of the $CO_2$ gas. Moreover, as the culture medium adjusting tank 23 is arranged in the second temperature control means (constant temperature bath) 19, the culture medium in the adjusting tank 23 is controlled substantially at a predetermined temperature. During cultivating operation, the temperature of the culture medium in the culture vessel is controlled with higher accuracy by means of the first temperature control means 13.

After the medium has been adjusted in the tank 23 for values such as pH, the medium is not immediately supplied into the culture vessel 11 (by keeping the valves AV9 and AV10 closed) and is circulated in the culture medium supply section 21 to bring it under a stable condition.

For the stabilizing operation of the culture medium, the medium in the culture medium adjusting tank 23 is first fed under a pressure difference into the second tank 25b through the flow passage 35, the valves AV8 and AV6 and the flow passage 33. The upper level of the culture medium in the second tank 25b is monitored by the level gauge LI3. After the medium in the tank 23 has been fed under a pressure difference into the second tank 25b, the valve AV6 is closed and the valve AV4 is opened. At this moment, the three-way valves SV2, SV3 and the like are opened to switch over the gas flow passages such that the second gas pressure is supplied from the second pressure chamber 63b into the first tank 25a and the first gas pressure is supplied from the first pressure chamber 63a into the second tank 25b. Moreover, the valve AV1 is closed, and the valves AV7 and AV3 are opened. Therefore, the culture medium is then fed under pressure difference from the second tank 25b into the medium adjusting tank 23 in which the parameters such as the pH are adjusted in the manner as above described. Then, the adjusted culture medium is fed under pressure difference into the first tank 25a through the flow passage 35, the valve AV7, the flow passage 36, the valve AV3 and the flow passage 31.

The culture medium is cyclically circulated between the medium adjusting tank 23 and the first and second tank 25a and 25b in the manner as above described to bring the temperature, pH and DO of the culture medium into predetermined values.

(4) Cell Inoculation Into the Culture Vessel

Then, for example, inoculation cells are poured into the culture chamber 11b through the inlet 15 of the hollow fiber 11 under an environment which has been treated so as not to contaminate the inoculation cells.

(5) Supplying the Culture Medium to the Culture Vessel

Then, the culture medium is supplied into the culture vessel. Such a supplying of the medium will be explained with reference to a case that in the supply section, for example, the first gas pressure is supplied into the first tank 25a and the second gas pressure is supplied into the second tank 25b, while the culture medium returning from the culture vessel 11 is restored or collected in the second tank 25b (the condition shown in FIG. 2B).

In this case, for the purpose of causing the culture medium to flow in two directions in the culture vessel, the culture medium in the first tank 25a is fed under a pressure difference through the adjusting tank 23 in the passage of the flow passage 35, the valve AV7, the flow passage 36, the valve AV9, the flow passage 37, the culture vessel 11, the flow passage 39, the valves AV10 and AV6, the flow passage 33 and the second tank 25b for a period of time during cell culture. For a next period of time, the culture medium in the first tank 25a is fed under pressure difference through the adjusting tank 23 in the passage of the flow passage 35, the valve AV8, the flow passage 38, the valve AV10, the flow passage 39, the culture vessel 11, the flow passage 37, the valve AV9, the flow passage 42, the valve AV5, the flow passage 33 and the second tank 25b. In this manner, the culture medium is caused to flow in two directions in which the medium enters one side of the culture vessel and leaves the other side of the vessel, and enters on the other side and leaves the one side of the vessel. The number of times of switching over the directions and the length of the period of the switching over are appropriately determined according to the culture cells. Directions in which the culture medium is fed into the culture vessel are changed with time intervals.

Moreover, when the culture medium supplied into the culture vessel is collected into the second tank 25b and its upper surface arrives at the upper limit level in the second tank 25b, the culture medium flow passages as above described are switched over such that the second gas is supplied into the first tank 25a, while the first gas is supplied into the second tank 25b to collect the culture medium returning from the culture vessel 11 into the first tank 25a. In this manner, the culture medium supply can be effected in the same manner as above described.

Furthermore, the culture medium can be fed under a pressure difference in one direction without switching over the flowing directions of the culture medium in the culture vessel.

(6) Sampling of Culture Substances and the Like During the Period of Cultivating Sampling is carried out in a manner described herein for proliferation of the culture substance and estimation of product in this embodiment.

In a mode of supplying the culture medium into the culture vessel, the valve AV9 (or AV10) downstream of the flow of the culture medium in the culture vessel 11 is closed, and the valve MV1 between the outlet 17 of the culture vessel 11 and a product receiving tank 91 is opened. As a result, a pressure difference occurs between the culture medium adjusting tank 23 and the product receiving tank 91, so that the product in the culture chamber 11b is fed together with the culture medium under a pressure difference into the product receiving tank 91. The cells and products sampled in this manner are observed with microscopes for the cells and with reagents dependent upon the products.

Moreover, on the basis of such an observation of the culture medium, change in pH and consumed amount of DO, the time to exchange the culture medium is determined. The culture medium is replaced with a new one according to the obtained time. Further, part of the culture medium is sampled through the passage of the adjusting tank 23, the flow passage 47, the valve AV13 and the sterilization filter F7. Metabolites such as, for example, glucose, lactic acid and like in the sampled culture medium are estimated to find the consumed components and the change in waste matter in addition to the above observations. The results of the estimation may be used to determine the exchanging time of the culture medium.

Modification

It is evident that this application is not limited to the above embodiments.

Figure 3:
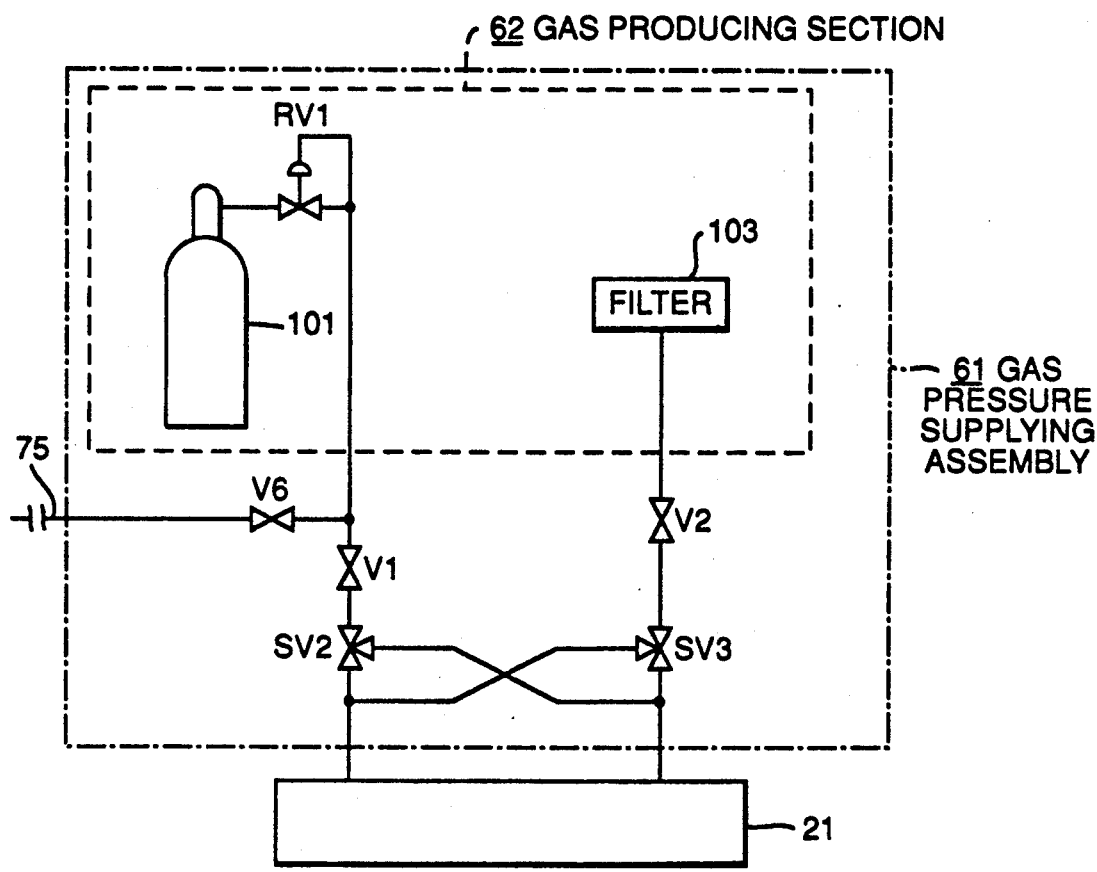
FIG. 3 is a block diagram illustrating a modification of a gas pressure supply section according to the invention.

For example, the gas pressure producing section 62 of the gas pressure supply assembly 61 has been shown constructed by the first and second pressure chambers 63a and 63b, the compressor 65, a plurality of valves and the pressure regulator in the above embodiment. However, the gas pressure producing section 62 may be constructed as shown in FIG. 3 in a simpler manner such that it includes a high pressure gas bomb 101 and a pressure regulator and a valve V2 on the lower pressure side which is directly connected to the atmospheric pressure without providing a low pressure chamber. With this arrangement, it is preferable to provide a filter having open mesh at an inlet for introducing the air to protect the sterilization filters F2 and F3. In a factory having an installation supplied with a high pressure gas, for example, air, nitrogen or the like, the gas pressure may be obtained from such an installation.

Moreover, the gas to be introduced into the gas supply assembly is not limited to air. Other suitable gases, for example, nitrogen, argon or the like or a mixture of these gases may be used.

In the above embodiment, the culture medium supply assembly which has been explained is provided with the culture medium adjusting tank 23. However, the culture medium adjusting tank may be removed from this arrangement, and instead thereof the pH and the like may be adjusted in the culture medium supply and collection tank or in the flow passages of the culture medium.

Figure 2C:
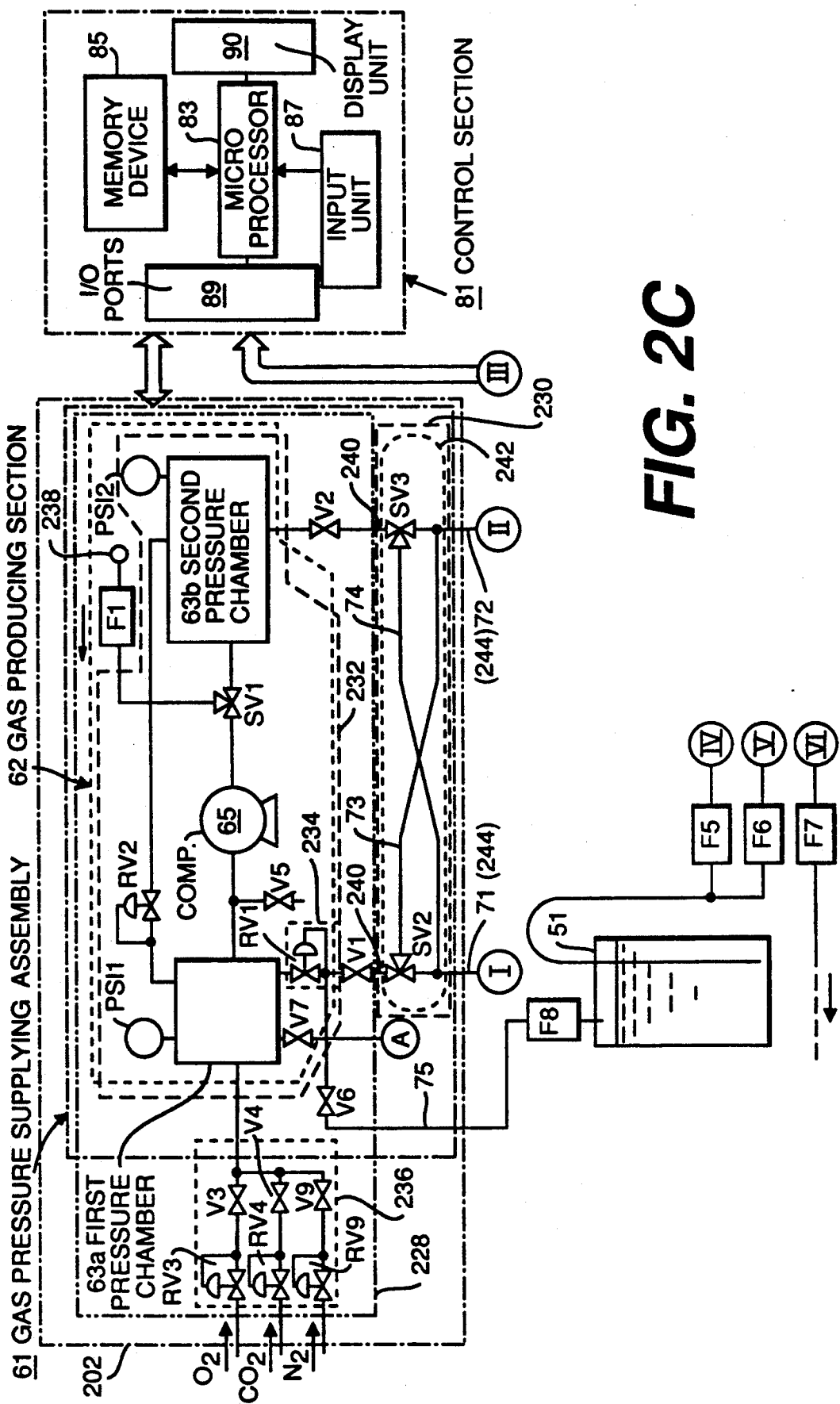
Figure 2D:
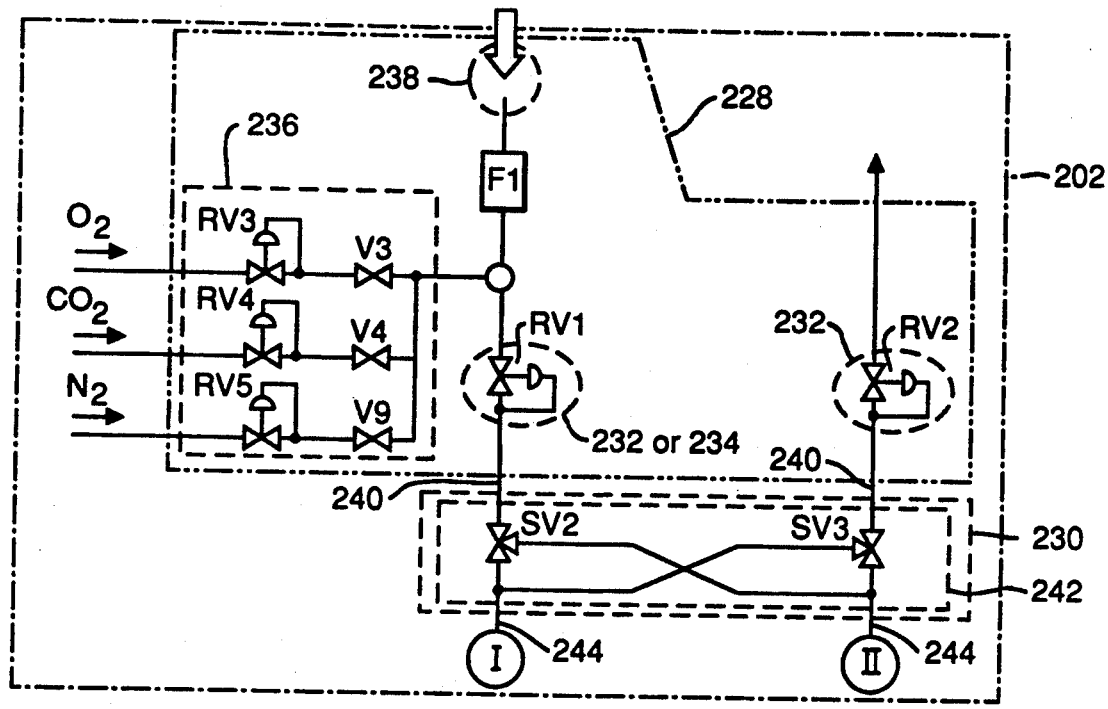
Figure 2E:
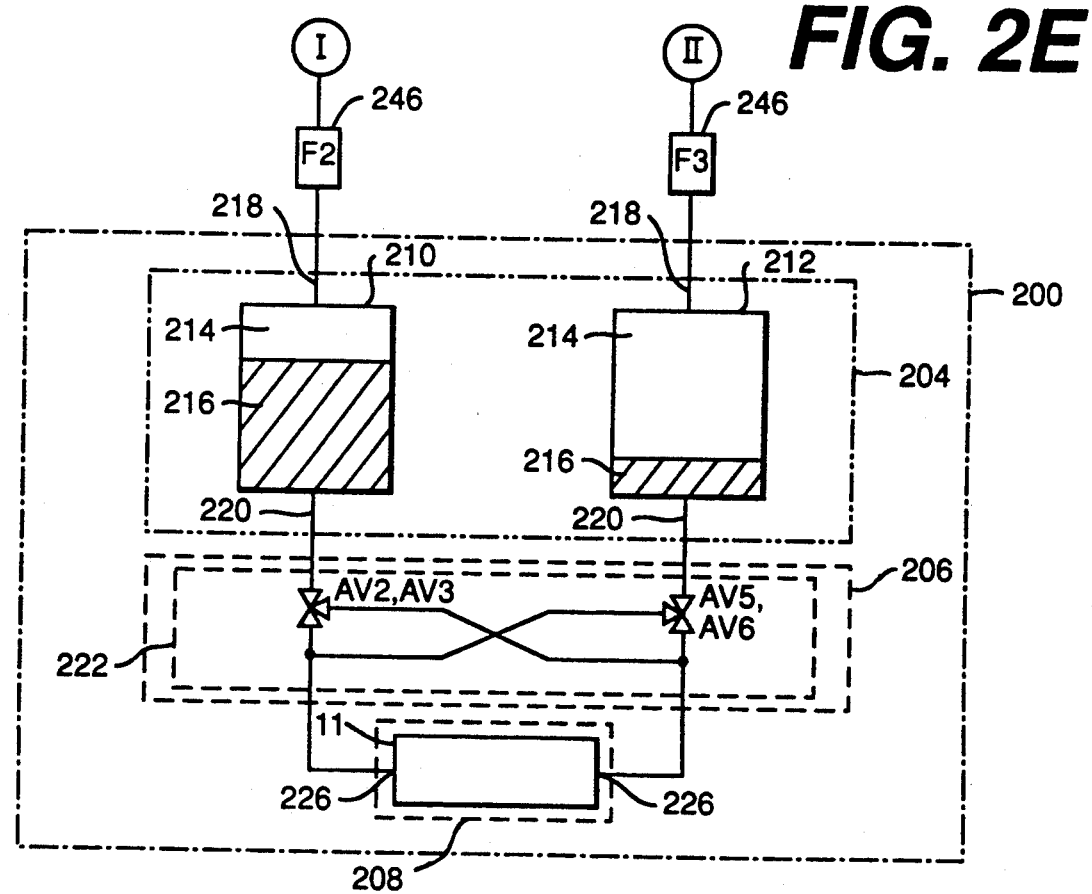

In this embodiment a culture system comprises a culture medium supply assembly 200 (FIGS. 2B and 2E) and a gas supply assembly 202 (FIGS. 2C and 2D). The culture medium supply assembly comprises a culture medium supply and collection tank section 204 (FIG. 2E), a culture medium flow passage switching-over section 206 (FIG. 2E) and a culture section 208 (FIG. 2E). The culture medium supply and collection tank section 204 has provided therein at least first and second tanks 210, 212 (FIG. 2E) for supplying and collecting the culture medium, respectively. Each of the tanks 210, 212; 25a, 25b has therein a gas phase 214 (FIG. 2E) and a culture medium phase 216 (FIG. 2E). And further, each of the tanks has provided thereto at least one gas port 218 (FIG. 2E) connected to the gas phase 214 and at least one culture medium port 220 (FIG. 2E) connected to the culture medium phase 216. The culture medium flow passage switching-over section 206 comprises first switching-over means 222 (FIG. 2E) for selecting a culture medium flow passage between the first and second tanks and the culture section. The culture section 208 comprises at least one culture vessel 11 (FIG. 2E). The culture vessel has provided thereto two culture medium ports 226 (FIG. 2E). One of the culture medium ports 226 is connected to the culture medium port 220 of the first tank 210 through the culture medium flow passage switching-over section 206 and the other to the culture medium port 220 of the second tank 212 through the switching-over section 206. The gas supply section 202 comprises a gas control section 228 (FIGS. 2C and 2D) and a gas flow passage switching-over section 230 (FIGS. 2C and 2D). The gas control section 228 has provided therein gas pressure regulating means 232 (FIGS. 2C and 2D), gas flow rate regulating means 234 (FIGS. 2C and 2D), gas component regulating means 236 (FIGS. 2C and 2D) and gas source switching-over means 238 (FIG. 2D). The gas control section 228 has also provided thereto at least two gas ports 240 (FIGS. 2C and 2E). The gas flow passage switching-over section 230 comprises second switching-over means 242 (FIGS. 2C and 2D) for selecting a gas flow passage 244 (FIGS. 2C and 2D) between the gas control section 228 and the first and second tanks 210, 212 (FIG. 2E). The gas flow passage switching-over section 230 is connected to the gas ports 240 of the gas control section 228 and to the gas port 218 of the first and second tanks 210, 212 of the culture medium supply section 200.

In accordance with one preferred example, using the gas pressure regulating means 232, a pressure difference is produced between the at least two gas ports 240 of the gas control section 228 so as to cause the transfer of the culture medium between the first and second tanks 210 and 212, while connecting one of the gas ports 240 of the gas control section 228 to the gas phase through the gas port 218 of the first tank 210 and the other gas port 240 to the gas phase through the gas port 218 of the second tank 212 by the use of the second switching-over means 242. Then the level change of the culture medium phase 216 in the first and second tanks 210 and 212 is caused by the transfer of the culture medium. In accordance with the level change, the gas flow passages to the gas ports 218 connected to the first and second tanks 210 and 212 are repeatedly switched-over each other by the second switching-over means 242 thereby for continuously feeding the culture medium to the culture vessel 11 of the culture section 208.

Further, in accordance with another preferred example, using the gas flow rate regulating means 234, a constant amount of the gas is supplied from at least one of the gas ports 240 of the gas control section 228 to the first or second tank 210 or 212 through the corresponding gas port 218 so as to cause the transfer of the culture medium between the first and second tanks 210 and 212. Then, the level changes of the culture medium phase 216 in the first and second tanks 210 and 212 caused by the transfer of the culture medium. In accordance with the level change, the gas flow passages to the gas ports 218 connected to the first and second tanks 210 and 212 are repeatedly switched-over each other by the second switching-over means 242 thereby for continuously feeding the culture medium to the culture vessel 11 of the culture section 208.

According to another preferred example, using the gas pressure regulating means 232, the pressure difference between at least two gas ports 240 of the gas control section 228 is changed to set the amount of the culture medium fed to the culture vessel 11 to a suitable one.

According to a further preferred example, using the gas flow rate regulating means 234, the gas flow rate is changed to set the amount of the culture medium fed to the culture vessel 11 to a suitable one.

According to another preferred example, using the gas pressure regulating means 232, gas pressure at the respective gas ports 240 of the gas control section 228 is regulated to control dissolved gas concentration of the culture medium fed to the culture vessel 11, while maintaining the constant pressure difference between the respective gas ports 240.

Further, in another preferred example, using the gas pressure regulating means 232, gas pressure of the gas phase 214 in one of the first and second tanks 210 and 212 is regulated to control dissolved gas concentration of the culture medium fed to the culture vessel 11, while maintaining the constant amount of the gas flow fed to the gas phase 214 in the other of the tanks 210 and 212.

Further, in accordance with another preferred example, using the gas component regulating means 236, gas component of a gas phase in one of the first and second tanks 210 and 212, the gas phase having a higher gas pressure than the other of the tanks 210 and 212, is regulated to control the dissolved gas concentration of the culture medium fed to the culture vessel 11.

According to another preferred example, using the gas source switching-over means 238, a sort of gas fed to a gas phase in one of the first and second tanks 210 and 212, the gas phase having a higher gas pressure than the other of the tanks 210 and 212, is switched-over to control the dissolved gas concentration of the culture medium fed to the culture vessel 11.

Further, according to another preferred example, the culture medium flow passage switching-over section 206 comprises two culture medium flow passages. One of the culture medium flow passages is connected at its one end to one of the culture medium ports 220 of the first tank 210 and its other end to one of the culture medium ports 226 of the culture vessel 11. The other of the culture medium flow passage is connected at its one end to one of the culture medium ports 220 of the second tank 212 and at its other end to the other of the culture medium ports 226 of the culture vessel 11.

In accordance with another preferred example, the culture medium flow passage switching-over section 206 has provided therein switching-over means 222 for feeding the culture medium in one direction to the culture vessel 11.

According to another preferred example, at least one filter means 246 for filtering out at least undesirable bacillus is connected between the culture medium supply assembly 200 and the gas supply assembly 202.

According to another preferred example, the culture system may further comprise a culture medium regulating section 250 (FIG. 2B) having provided therein a culture medium regulating tank 252 (FIG. 2B) and means for regulating the culture medium. The culture medium regulating tank 252 has inside thereof a gas phase 254 (FIG. 2B) and a culture medium phase 256 (FIG. 2B) and is provided with at least one gas port 258 (FIG. 2B) connected to the gas phase 254 and at least two culture medium ports 260 (FIG. 2B) connected to the culture medium phase 256. The gas port 258 is connected to the gas control section 228 and the culture medium port 260 to the culture medium flow passage switching-over section 206. The gas control section 228 comprises portions 217 (FIG. 2A) and 236 (FIG. 2B).

In accordance with another preferred embodiment, using the gas component regulating means 236, a gas component of the gas phase 254 in the culture medium regulating tank 252 is regulated to control the dissolved gas concentration of the culture medium fed to the culture section 208.

Regarding FIGS. 2A and 2B, the gas supply section 202 comprises the gas pressure supplying section 61 and the gas component regulating means 236.

Further, the culture system of the above embodiment has been shown provided with means for adjusting the pH, DO and temperature of the culture medium. However the culture system according to the invention may be provided with means for adjusting other parameters, for example, dissolved concentration of $CO_2$ and the like depending upon the material to be cultivated.

Moreover, the supply of the culture medium, the removal of products and the like may be effected in a suction mode with negative pressure. An embodiment for supplying the culture medium from the replenishing tank 51 into the first tank 25a in the suction mode will be briefly explained.

In this embodiment, the flow passage 75 between the sterilization filter F8 and the valve V6 is removed and one end of the filter F8 on the side opposite to the replenishing tank 51 is opened or exposed to the atmosphere.

The three-way valve SV1 is switched over onto the side of the second pressure chamber 63b and the compressor 65 is operated. Then the valve V5 is opened and the valve V1 is closed, and the air in the second pressure chamber 63b is forced out of the system through the valve V5 to bring the second pressure chamber 63b into negative pressure. The respective valves are then switched over so that the system of the second pressure chamber 63b, the valve V2, the three-way valve SV3, the flow passages 74 and 71, the filter F2, the first tank 25a and the flow passage 46 become effective. The valve AV12 is then opened so that the culture medium in the replenishing tank 51 is fed under pressure difference into the first tank 25a in the suction mode.

After starting the feeding under a pressure difference, the liquid level of the culture medium in the first tank 25a is monitored by the level gauge LI1 of the tank. When the level gauge LI1 detects the fact that the medium has arrived at its upper limit level, the valves AV12 and V2 are closed.

Then, the gas pressure producing assembly is brought into a condition similar to the culture medium supplying condition above described. Thereafter, the respective valves are switched over so that the flow system becomes effective. The flow system consists of the first pressure chamber 63a, the valves RV1, V1, and SV2, the flow passage 71, the filter F2, the first tank 25a, the flow passage 31, the valve AV1, the flow passage 32, the culture medium adjusting tank 23, the flow meter 27, the flow passage 35, the valve AV8, the flow passages 38 and 44, the valve AV6, the flow passage 33, the second tank 25b, the filter F3, the flow passage 72, the valves SV3 and V2 and the second pressure chamber 63b. Therefore, the culture medium in the first tank 25a is supplied through the adjusting tank 23 into the second tank 25b. The amount of the culture medium fed into the second tank 25b is monitored by the level gauge LI3. When the liquid surface has arrived at the lower limit level, the above flow system is completely closed so that the gas producing section is returned to the suction mode as above described, whereby the culture medium in the culture medium replenishing tank 51 is replenished into the first tank 25a in the same manner as above described. The amount of the culture medium in the first tank 25a is monitored by the level gauge LI1. When the liquid surface of the medium has arrived at the upper limit level, the valve AV12 is closed. The liquid surfaces of the medium replenished in the first tank 25a, the second tank 25b and the culture medium adjusting tank 23 as above described are shown in FIG. 2B. The replenishing of the culture medium can be effected in the suction mode in this manner.

The culture medium supply assembly and the gas pressure producing assembly according to the invention are not limited to the above embodiments and various modifications may be made depending upon supplying methods of the culture medium.

Figure 4A:
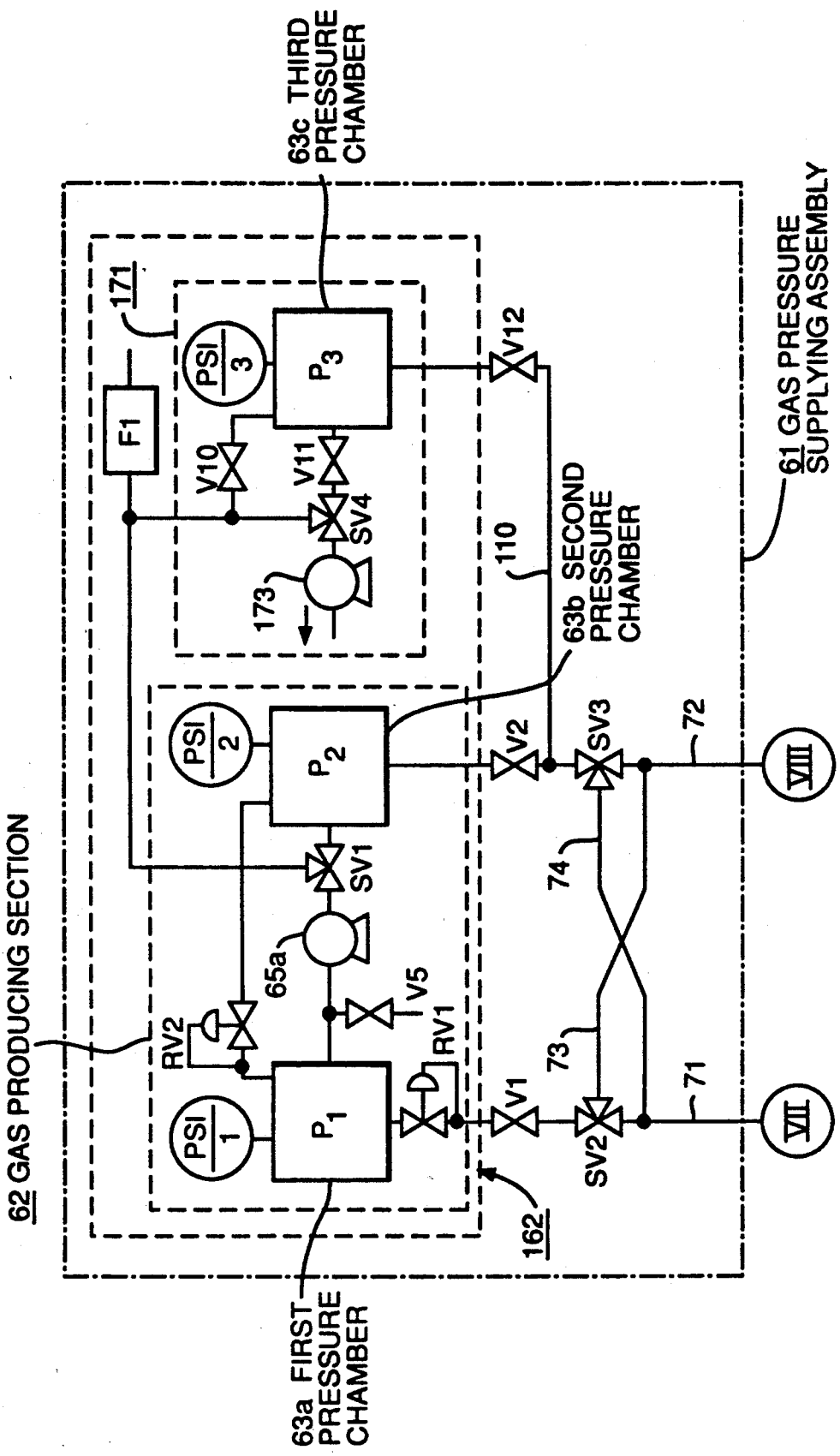
FIGS. 4A and 4B are block diagrams illustrating respective parts of a principal portion of another embodiment of a culture system according to the invention.
Figure 4B:
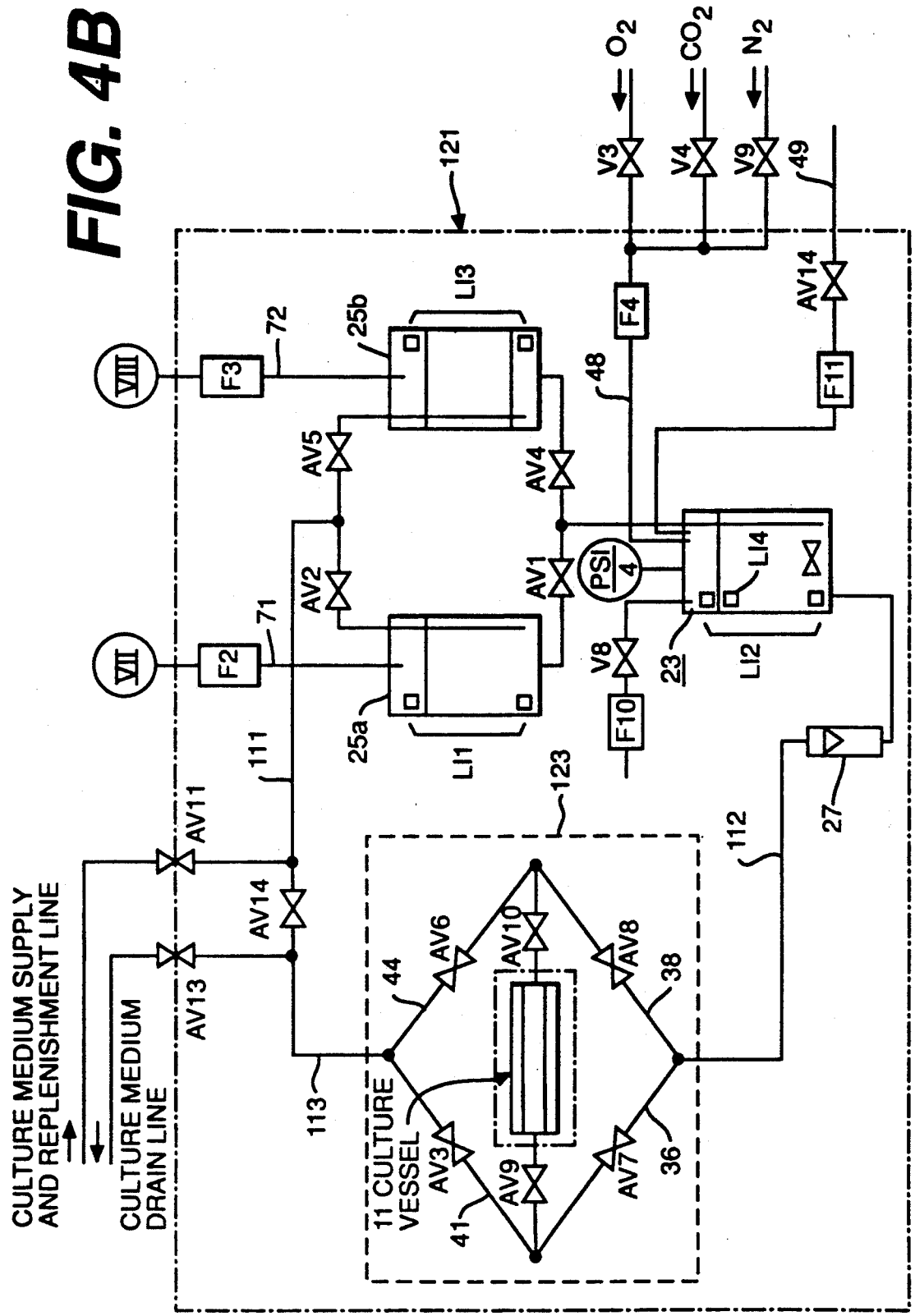

For example, the culture system may be constituted as shown in FIGS. 4A and 4B to provide for the following features, in that a culture medium is continuously introduced from outside of the culture system thereinto and continuously supplied into the culture vessel and further continuously drained out of the culture system, that a culture medium is continuously supplied into the culture vessel, while part of the culture medium is circulated in the culture system or drained out of the culture system, and that a culture medium is circulated in the culture system, while part of culture medium is drained out of the culture system or is replenished from outside of the culture system.

FIGS. 4A and 4B are schematic block diagrams of respective parts of a principal portion of a culture system capable of supplying and circulating the culture medium in this manner. In FIGS. 4A and 4B, like components are designated by the same reference numerals as those in FIGS. 2A and 2B, while components not essential for an understanding of the embodiment, for example, control section 81, detailed parts and the like are deleted.

In FIG. 4A, reference numeral 162 denotes a gas pressure producing assembly in the modified culture system. The gas pressure producing assembly 162 comprises a negative gauge pressure producing section 171 in addition to the component designated by 62 in FIG. 2A. The negative gauge pressure producing section 171 comprises a vacuum pump 173, a third pressure chamber 63c, a three-way valve SV4, magnetic valves V10 and V11, and a pressure indicator PSI 3 with a pressure switch. The vacuum pump 173 is controlled depending upon a set value of the pressure indicator PSI 3 to maintain the gas pressure in the third pressure chamber 63c at a desired negative gauge pressure. The third pressure chamber 63c is connected through a gas flow passage 110 having a magnetic valve V12 to the flow passage 72 (already explained) between the valves V2 and the three-way valve SV3.

The compressor, the vacuum pump and the valves of the gas pressure producing assembly 162 are operated so that pressures P1, P2 and P3 in the first, second and third pressure chambers 63a, 63b and 63c are maintained in a relation of P1>P2>atmospheric pressure>P3.

With the culture system including the gas pressure producing assembly 162, the three-way valves SV2 and SV3 are switched over to provide four conditions such that (1) the gas pressure P1 is supplied into the first tank 25a and the gas pressure P2 is supplied into the second tank 25b, (2) the pressure P2 is supplied into the first tank 25a and the pressure P1 is supplied into the second tank 25b, (3) the pressure P1 is supplied into the first tank 25a and the pressure P3 is supplied into the second tank 25b, and (4) the pressure P3 is supplied into the first tank 25a and the pressure P1 is supplied into the second tank 25b.

A modified culture medium supply assembly 121 is shown in FIG. 4B. The culture medium supply assembly 121 is fundamentally similar to the culture medium supply assembly 21 shown in FIG. 2B with the exception that arrangements of the culture medium flow passages and valves are different from those shown in FIG. 2B.

In this embodiment, the culture medium is supplied through a flow passage 111 shown in FIG. 4B into the first tank 25a or the second tank 25b. The culture medium in the first tank 25a or second tank 25b is further caused to flow through a culture medium adjusting tank 23, a flow meter 27, a flow passage 112, a flow direction switch-over bypass block 123 (referred to hereinafter as a "switch-over block"), and a flow passage 113.

The switch-over block 123 is constructed as follows. A loop-shaped flow passage is formed by a flow passage 36 having a valve AV7, a flow passage 38 having a valve AV8, a flow passage 41 having a valve AV3, and a flow passage 44 having a valve AV6. The flow passage 112 is connected to a connection between the flow passages 36 and 38, and the flow passage 113 is connected to a connection between the flow passages 41 and 44. Moreover, between the connection of the flow passages 36 and 41 and connection of the flow passages 38 and 44, there is provided a system consisting of a valve AV9, a culture vessel 11 and a valve AV10. Therefore, these valves are switched over according to objects so that in this switch-over block, the flow directions of the culture medium can be switched over and the culture medium can be circulated without supplying new culture medium into the culture vessel 11 in the similar manner explained with reference to FIG. 2B. These passages are for supplying the culture medium into the culture vessel 11 in order of the flow passage 112, the valves AV7 and AV9, the culture vessel 11, the valve AV10 and AV6, and the flow passage 113 or the flow passage 112, the valves AV8 and AV10, the culture vessel 11, the valves AV9 and AV3, and the flow passage 113. Moreover, the other passages are for bypassing the culture vessel 11 through the flow passage 112, the valves AV7 and AV3, and the flow passage 113 or flow passage 112, the valves AV8 and AV6, and the flow passage 113.

In this embodiment, the switch-over block is constructed as follows. The first and second flow passages 36 and 41 having the valves AV7 and AV3 are connected in series with each other. The third and fourth passages 38 and 44 having the valves AV8 and AV6 are connected in series with each other. The first and second flow passages 36 and 41 in series connected and the third and fourth flow passages 38 and 44 in series connected are connected in parallel in the flow passage consisting of the flow passages 112 and 113. The fifth flow passage having the valve AV9 is connected between one end of the culture vessel 11 and the connection between the first and second flow passages 36 and 41. The sixth flow passage having the valve AV10 is connected between the other end of the culture vessel 11 and the connection between the third and second flow passages 38 and 44.

Examples of culture systems shown in FIGS. 4A and 4B will be concretely explained with regard to a mode of feeding culture mediums hereinafter.

EXAMPLE 1

In this case, a culture medium is continuously introduced into the culture system from the outside thereof, is continuously fed into the culture vessel 11, and is further continuously drained out of the culture system.

The respective valves are operated so that the gas pressure P1 is supplied to the first tank 25a and the gas pressure P3 is supplied to the second tank 25b. Then the passage of the valve AV11, the flow passage 111, the valve AV5, and the second tank 25b is made effective, so that a culture medium is fed under pressure difference in suction mode from the outside of the culture system through a culture medium supply replenishing line on a primary side of the valve AV11 into the second tank 25b. On the other hand, the passage of the first tank 25a, the valve AV1, the culture medium adjusting tank 23, the flow meter 27, the flow passage 112, the switch-over block 123, the flow passage 113 and the valve AV3 is made effective, so that the culture medium in the first tank 25a is drained under a pressure difference in positive pressure mode through the above passage out of the culture system.

Moreover, respective valves are opened so that the gas pressure P3 is supplied into the first tank 25a and the gas pressure P1 is supplied into the second tank 25b. Then the passage of the valve AV11, the flow passage 111, the valve AV2 and the first tank 25a is made effective, so that the culture medium is fed under pressure difference in suction mode from the outside of the culture system into the first tank 25a. On the other hand, the passage of the second tank 25b, the valve AV4, the culture medium adjusting tank 23, the flow meter 27, the flow passage 112, the switch-over block 123, the flow passage 113 and the valve AV13 is made effective, so that the culture medium in the second tank 25b is drained under pressure difference in positive pressure mode through the above passage including the switch-over block out of the culture system.

The two passages for supplying and draining the culture medium as above described are used by switching them over under the monitoring of the level gages LI1–LI3. The supply and drain of the culture medium according to Example 1 are carried out in this manner.

EXAMPLE 2

In this case, a culture medium introduced in the culture system is continuously circulated.

The introduction of the culture medium into the culture system is effected in the same manner as explained in Example 1. The explanation thereof will not be described in further detail.

The respective valves are operated so that the gas pressure P1 is supplied into the first tank 25a and the gas pressure P2 is supplied into the second tank 25b. Moreover, the passage of the first tank 25a, the valve AV1, the culture medium adjusting chamber 23, the flow meter 27, the flow passage 112, the switch-over block 123, the flow passage 113, the valve AV14, the flow passage ill, the valve AV5 and the second tank 25b is made effective, so that the culture medium in the first tank 25a is fed under a pressure difference in a positive mode into the second tank 25b through the above passage including the switch-over block 123.

The respective valves are operated so that the gas pressure P2 is supplied into the first tank 25a and the gas pressure P1 is supplied into the second tank 25b. Moreover, the passage of the second tank 25b, the valve AV4, the culture medium adjusting chamber 23, the flow meter 27, the flow passage 112, the switch-over block 123, the flow passage 113, the valve AV14, the flow passage 111, the valve AV2, and the first tank 25a is made effective, so that the culture medium in the second tank 25b is fed under a pressure difference in a positive mode into the first tank 25a through the above passage including the switch-over block 123.

The two culture medium supply and drain passages above described are used by switching over these passages under the monitoring by the level gauges LI1, LI3 to accomplish the circulation and feeding under pressure difference of the culture medium according to the method of Example 2. During the circulation in this manner, the valve AV13 is opened and closed in accordance with requirements, so that part of the circulating culture medium can be drained out of the culture system without stopping the supply of the culture medium into the culture vessel 11.

Further, by properly switching over the operations of Examples 1 and 2 above described, the culture medium can be replenished from the outside of the culture system into the culture system without stopping the supply of the culture medium to the culture vessel.

In this manner, continuous feeding of the medium is also possible according to the supply method of the culture medium according to the invention.

Although the gas pressure producing source has been explained as the compressor and vacuum pump, they are only by way of example, and other sources of gas under pressure such as pipe lines in a factory or compressed gas bombs could be used.

Furthermore, the culture medium supply assembly and the gas pressure supply assembly shown in the above embodiments and modifications could be variously changed without departing from the spirit and scope of the invention.

In carrying out the culture medium supply method or the culture system according to the invention, various culture cells may be used such as those anchoring on the hollow fiber or suspending in the culture chamber. Further, the supply of the culture medium to the culture vessel can be effected in a condition that the direction of flow of the culture medium in the culture system is fixed or periodically changed in opposite directions.

For example, when cells which tend to anchor to the hollow fibers or to be suspended in the chamber are cultivated by the culture medium supplied into the culture vessel in one direction or in two opposite directions, results shown in Table 1 will be obtained.

TABLE 1

| | Direction of culture vessel medium, in culture | |
|---|---|---|
| | One fixed direction | Two directions |
| Anchored cell | Cell density becomes higher in a zone upstream of the culture vessel. | Cell density is uniform over all zone in the culture vessel. |
| Suspended cell | Cell density becomes higher in a zone downstream of the culture vessel. | Cell density is uniform over all zone in the culture vessel. |

With the culture system according to the invention, moreover, various parameters for the operation can easily be controlled within very severe ranges as follows.

(a) Cultivating temperature—±0.1° C. with respect to a set temperature (b) DO Value—±0.1 ppm dependent upon proliferation amount of cells.

(c) pH value—±0.1 with respect to a set value.

As can be seen from the above explanation, according to the culture medium, supply method and the culture system of the invention, the culture medium is fed under a pressure difference of gas for supplying the medium into the culture vessel.

As a result, the culture medium can be supplied into the culture vessel stably and smoothly without any surge or pulse for a long period of time.

Moreover, the culture system according to the invention is easy to maintain and durable in use because there is no mechanically slidable part. Further, there is no part with which the culture medium is mechanically in contact. As a result, maintenance can be carried out without permitting impurities to enter the culture medium, even if the gas pressure supply section fails.

In supplying the culture medium into the culture vessel, the direction of flow of the culture medium in the culture vessel is changed in an opposite direction according to the invention. Therefore, the cultivating environment can be made uniform throughout the culture vessel so that the cultivating yield rate is improved.

Furthermore, by changing kinds of gas for feeding the culture medium under a pressure difference or adjusting components of the gas depending upon kinds of the culture substances, the cultivating yield ratio is further improved.

According to the culture medium supply method and the culture system of the invention, the cultivation is carried out with an efficiency much higher than that of the prior art to produce cells and substances beneficial for human beings as immunoglobulin such as monoclonal antibody and the like.

It is further understood by those skilled in the art that the foregoing description is that of preferred embodiments of the disclosed methods and apparatus and that various changes and modifications may be made in the invention without departing from the spirit and scope thereof.

What is claimed is:

1. A culture system, comprising:
   a culture medium supply section and a gas supply section;
   said culture medium supply section comprising a culture medium supply and collection tank section, a culture medium flow passage switching-over section and a culture section;
   said culture medium supply and collection tank section including at least first and second tanks for supplying and collecting a culture medium;
   each of said tanks including a gas phase and a culture medium phase;
   each of said tanks including at least one gas port connected to said gas phase and at least one culture medium port connected to said culture medium phase;
   said culture section comprising at least one culture vessel, said at least one culture vessel having provided thereto at least first and second culture medium ports;
   said culture medium flow passage switching-over section comprising first switching-over means, said first switching-over means including at least one culture medium port connected to said at least one culture medium port of said first tank, at least one culture medium port connected to said at least one culture medium port of said second tank, at least one culture medium port connected to said first culture medium port of said at least one culture vessel and at least one culture medium port connected to said second culture medium port of said at least one culture vessel;
   said first switching-over means having formed therein a plurality of culture medium flow passages connected between said culture medium ports connected to said tanks and said culture medium ports connected to said at least one culture vessel, said culture medium flow passages being constructed such that fluid communication is provided between said culture medium phase of said first tank and said culture medium phase of said second tank via said at least one culture vessel, a first configuration of said culture medium flow passages providing said fluid communication wherein culture medium flows through said at least one culture vessel from said first culture medium port of said at least one culture vessel to said second culture medium port of said at least one culture vessel and a second configuration of said culture medium flow passages providing said fluid communication wherein culture medium flows through said at least one culture vessel from said second culture medium port of said at least one culture vessel to said first culture medium port of said at least one culture vessel;
   said gas supply section comprising a gas control section and a gas flow passage switching-over section;
   said gas control section including at least two gas ports;
   said gas flow passage switching-over section comprising second switching-over means, said second switching-over means including at least two gas ports connected to said at least two gas ports of said gas control section respectively, at least one gas port connected to said at least one gas port of said first tank and at least one gas port connected to said at least one gas port of said second tank;
   said second switching-over means having formed therein a plurality of gas flow passages, a first configuration of said gas flow passages providing a gas pressure difference between said at least two gas ports of said gas control section such that culture medium flows from said first tank to said second tank and a second configuration of said gas flow passages providing a gas pressure difference between said at least two gas ports of said gas control section such that culture medium flows from said second tank to said first tank; and
   said gas control section including gas pressure regulating means for regulating gas pressures of said gas phases in said first and second tanks through said gas ports of said gas control section, gas flow rate regulating means for regulating gas flow rate of said gas phase in said first and second tanks through said gas ports of said gas control section, and gas component regulating means for regulating a volume percent of gas component of said gas phase in said first and second tanks through said gas ports of said gas control section.

2. A culture system according to claim 1, wherein said gas pressure regulating means produces a pressure difference between said at least two gas ports of said gas control section at a constant value so as to cause the transfer of the culture medium between said first and second tanks,
   wherein said second switching-over means repeatedly switches between said first configuration and said second configuration in accordance with level change of said culture medium phase in said first and second tanks caused by the transfer of the culture medium, thereby for continuously feeding the culture medium to said at least one culture vessel of said culture section.

3. A culture system according to claim 2, wherein said gas pressure regulating means changes said pressure difference between said at least two gas ports of said gas control section from said constant value to another constant value so as to set an amount of the culture medium fed to the at least one culture vessel from a level corresponding to said constant value to another level corresponding to said other constant value.

4. A culture system according to claim 2, wherein said gas pressure regulating means regulates gas pressures at said at least two gas ports of said gas control section to control a dissolved gas concentration of the culture medium fed to the at least one culture vessel, while maintaining said pressure difference between said at least two gas ports of said gas control section at said constant value.

5. The culture system according to claim 1, wherein said gas flow rate regulating means supplies a constant amount of gas from at least one of said gas ports of said gas control section to said first or second tank through the corresponding gas port, thereby causing a transfer of the culture medium between said first and second tanks, and
   wherein said second switching-over means repeatedly switches between said first configuration and said second configuration according to a level change of the culture medium phase in said first and second tanks caused by said transfer of the culture medium, thereby continuously feeding the culture medium to said at least one culture vessel of said culture section.

6. A culture system according to claim 5, wherein said gas flow rate regulating means changes said gas flow rate from said constant amount to another constant amount to change an amount of the culture medium fed to the at least one culture vessel from a level corresponding to said constant amount to a level corresponding to said other constant amount.

7. A culture system according to claim 5, wherein said gas pressure regulating means regulates a gas pressure of the gas phase in one of said first and second tanks to control dissolved gas concentration of the culture medium fed to the at least one culture vessel, while maintaining said constant amount of gas flow fed to said gas phase in the other of said tanks.

8. A culture system according to claim 1, wherein said gas component regulating means regulates said volume percent of said gas component of said gas phase in one of said first and second tanks to control a dissolved gas concentration of the culture medium fed to said at least one culture vessel, said gas phase in said one of said tanks having a higher gas pressure than the other of said tanks.

9. A culture system according to claim 1, wherein said at least one culture medium port of said first tank is connected to said first culture medium port of said at least one culture vessel bypassing said culture medium flow passage switching-over section, and
wherein said at least one culture medium port of said second tank is connected to said second culture medium port of said at least one culture vessel bypassing said culture medium flow passage switching-over section.

10. A culture system according to claim 1, wherein at least one filter means for filtering out at least undesirable bacillus is connected between said culture medium supply section and said gas supply section.

11. A culture system according to claim 1, further comprising a culture medium regulating section including a culture medium regulating tank and means for regulating the culture medium;
wherein said culture medium regulating tank has inside thereof a gas phase and a culture medium phase and includes at least one gas port connected to said gas phase and at least two culture medium ports connected to said culture medium phase;
said at least one gas port of said culture medium regulating section being connected to said gas component regulating means of said gas control section;
wherein said at least two culture medium ports of said culture medium regulating tank are connected to said culture medium flow passages of said first switching-over means such that culture medium flows from said first tank into said regulating tank prior to flowing into said at least one culture vessel when said culture medium flow passages are in a third configuration and culture medium flows from said second tank into said regulating tank prior to flowing into said at least one culture vessel when said culture medium flow passages are in a fourth configuration.

12. A culture system according to claim 11, wherein said gas component regulating means regulates said volume percent of said gas component of said gas phase in said culture medium regulating tank to control a dissolved gas concentration of the culture medium fed to said culture section.

13. A method of supplying a culture medium into a culture vessel in a system, said system comprising
a culture medium supply section and a gas supply section;
said culture medium supply section comprising a culture medium supply and collection tank section, a culture medium flow passage switching-over section and a culture section;
said culture medium supply and collection tank section including at least first and second tanks for supplying and collecting a culture medium;
each of said tanks including a gas phase and a culture medium phase;
each of said tanks including at least one gas port connected to said gas phase and at least one culture medium port connected to said culture medium phase;
said culture section comprising at least one culture vessel, said at least one culture vessel having provided thereto at least first and second culture medium ports;
said culture medium flow passage switching-over section comprising first switching-over means, said first switching-over means including at least one culture medium port connected to said at least one culture medium port of said first tank, at least one culture medium port connected to said at least one culture medium port of said second tank, at least one culture medium port connected to said first culture medium port of said at least one culture vessel and at least one culture medium port connected to said second culture medium port of said at least one culture vessel;
said first switching-over means having formed therein a plurality of culture medium flow passages connected between said culture medium ports connected to said tanks and said culture medium ports connected to said at least one culture vessel, said culture medium flow passages being constructed such that fluid communication is provided between said culture medium phase of said first tank and said culture medium phase of said second tank via said at least one culture vessel, a first configuration of said culture medium flow passages providing said fluid communication wherein culture medium flows through said at least one culture vessel from said first culture medium port of said at least one culture vessel to said second culture medium port of said at least one culture vessel and a second configuration of said culture medium flow passages providing said fluid communication wherein culture medium flows through said at least one culture vessel from said second culture medium port of said at least one culture vessel to said first culture medium port of said at least one culture vessel; at least two gas ports;
said gas flow passage switching-over section comprising second switching-over means, said second switching-over means including at least two gas ports connected to said at least two gas ports of said gas control section respectively, at least one gas port connected to said at least one gas port of said first tank and at least one gas port connected to said at least one gas port of said second tank;
said second switching-over means having formed therein a plurality of gas flow passages, a first configuration of said gas flow passages providing a gas pressure difference between said at least two gas ports of said gas control section such that culture medium flows from said first tank to said second tank and a second configuration of said gas flow passages providing a gas pressure difference between said at least two gas ports of said gas control section such that culture medium flows from said second tank to said first tank; and said gas control section including gas pressure regulating means for regulating gas pressures of said gas phases in said first and second tanks through said gas ports of said gas control section, gas flow rate regulating means for regulating gas flow rate of said gas phase in said first and second tanks through said gas ports of said gas control section, and gas component regulating means for regulating a volume percent of gas component of said gas phase in said first and second tanks through said gas ports of said gas control section;

said method comprising the steps of:
a) connecting one of said gas ports of said gas control section to said at least one gas port connected to said gas phase of said first tank and connecting another gas port of said gas control section to said at least one gas port connected to said gas phase of said second tank by adjusting said gas flow passage switching-over section;

b) producing a sufficient gas pressure difference between said at least two gas ports of said gas control section to cause the culture medium to transfer between said first and second tanks; and c) alternating said gas pressure difference by switching between said first and second configurations of said gas flow passages in response to changes in levels in said first and second tanks caused by the transfer of said culture medium, thereby continuously feeding culture medium to said at least one culture vessel.

14. The method according to claim 13, further comprising the steps of:

causing a transfer of the culture medium between said first and second tanks by supplying, with said gas flow rate regulating means, a constant flow rate of gas pressure from at least one of said gas ports of said gas control section to a corresponding gas port connected to said first or second tank; and continuously feeding the culture medium to said at least one culture vessel of said culture section wherein said second switching-over means repeatedly switches between said first and second configurations of said gas flow passages in response to a change in the level of the culture medium phase in said first and second tanks caused by said transfer of the culture medium.

15. A method according to claim 14, wherein said gas pressure regulating means regulates a gas pressure at one of said gas ports of said gas control section to control dissolved gas concentration of the culture medium fed to said at least one culture vessel, while maintaining said constant flow rate to either of said gas ports of said gas control section.

16. A method according to claim 13, further comprising changing said gas pressure difference between said at least two gas ports of said gas control section to control the amount of culture medium fed to said at least one culture vessel.

17. A method according to claim 16, wherein said gas flow rate regulating means changes said gas flow rate to set an amount of the culture medium fed to said at least one culture vessel to a desired level.

18. A method according to claim 13, further comprising regulating gas pressures at the gas ports of the gas control section to control a concentration of gas dissolved within the culture medium fed to said at least one culture vessel while maintaining said gas pressure difference between said gas ports of said gas control section at a constant value.

19. A method according to claim 13, further comprising regulating said volume percent of said gas component of said gas phase in one of said tanks having a higher gas pressure by said gas component regulating means to control a concentration of gas dissolved in the culture medium fed to said at least one culture vessel.

* * * * *